United States Patent
Sato

[11] Patent Number: 6,149,618
[45] Date of Patent: Nov. 21, 2000

[54] TIGHTENING TOOL FOR MUSCLE TRAINING AND MUSCLE TRAINING METHOD USING SAME

[75] Inventor: Yoshiaki Sato, Fuchu, Japan

[73] Assignee: Best Life Co., Ltd., Tokyo, Japan

[21] Appl. No.: 08/257,147

[22] Filed: Jun. 9, 1994

[30] Foreign Application Priority Data

Nov. 22, 1993 [JP] Japan ................................ 5-313949

[51] Int. Cl.$^7$ .................................................. A61L 15/00
[52] U.S. Cl. ............................................ 602/75; 606/203
[58] Field of Search .................................. 606/201, 202, 606/203; 602/75, 62; 482/105, 124, 125, 126, 139; 128/876

[56] References Cited

U.S. PATENT DOCUMENTS

| | | | |
|---|---|---|---|
| 2,660,174 | 11/1953 | Saemann | 606/202 |
| 4,027,666 | 6/1977 | Marx | 602/62 |
| 4,273,328 | 6/1981 | Ozbey et al. | 272/137 |
| 5,015,251 | 5/1991 | Cherubini | 606/203 |
| 5,152,302 | 10/1992 | Fareed | 602/62 X |
| 5,219,356 | 6/1993 | Harreld et al. | 606/203 |
| 5,338,290 | 8/1994 | Aboud | 602/75 |

FOREIGN PATENT DOCUMENTS

| | | | |
|---|---|---|---|
| 0408049 | 1/1991 | European Pat. Off. | A61B 17/12 |
| 60-180459 | 11/1985 | Japan | A63B 21/02 |
| 242303 | 11/1990 | Japan | A63B 21/065 |
| 9205741 | 4/1992 | WIPO | A61B 17/12 |

OTHER PUBLICATIONS

Article entitled "Sports Medicine" ed. Eiichiro Hisamatsu and Michio Ikai, (K.K. Kyorin Shoin & Taiiku-no-kagakusha, Sep. 20, 1967) 4th ed.pp. 203–206.

*Primary Examiner*—Kim M. Lee
*Attorney, Agent, or Firm*—Michael D. Bednarek; Crowell & Moring LLP

[57] ABSTRACT

A tightening tool 1 including an elastic body 2 in the form of a belt, rope, tube, etc. for forming a tightening loop L adapted to surround a desired part of muscles and tighten it, and locking means 3 for holding the tightening loop L at a desired size. A muscle training method for accelerating enlargement and strengthening of the muscles can be practiced by the tightening tool to temporarily block the flow of blood to the desired part of the muscles.

1 Claim, 2 Drawing Sheets

TIGHTENING TOOL FOR MUSCLE TRAINING AND MUSCLE TRAINING METHOD USING SAME

BACKGROUND OF THE INVENTION

1. Field of the Prior Invention

The present invention relates to an accessory tool to be used for muscle training and also to a muscle training method using the accessory tool.

2. Description of the Prior Art

In performing muscle training, a training effect is generally obtained by applying a load to a desired part of muscles with use of a weight such as a dumbbell or barbell, or a resistance based on an elasticity of a spring, rubber, etc., and by carrying out exercise to stretch and contract the desired part of muscles in such a loaded condition to such a degree as to obtain a given fatigue. According to this muscle training, the training effect is improved only by increasing the weight or the resistance of the training tool or by increasing the number of times of the exercise to the muscles. However, even when the load to the desired part of muscles is unduly increased, an increased quantity of the load is dispersed to another part of muscles. As a result, the other part of muscles is undesirably strengthened, and in some cases, the muscles or joints may be damaged.

Many studies on the relationship between sports and muscles have been made from the viewpoint of sport medicine with various themes such as the determination of causes of muscle fatigue, the growth of muscles, and the relationship between muscles and load. As the result of these studies, it is known that the muscles are fatigued as soon as the flow of blood is blocked, that isometric muscle contraction caused by lifting or supporting a heavy object is more effective for enlargement of the muscles than isotonic muscle contraction caused by running or swimming, and that a muscular strength is developed rather by applying a load at a given level or more. Moreover, it is also known that exercise with the flow of blood kept blocked remarkably enhances muscular strength though a fundamental mechanism thereof has not yet been clarified [see "Sports Medicine", ed. Eiichiro Hisamatsu and Michio Ikai, (K. K. Kyorin Shoin and Taiiku-no-kagakusha, Sep. 20, 1967) 4th ed., pp 203 and 206].

The present inventor has long been concerned with the study of muscle training to search for an effective training tool and a training method using it. Then, the present inventor has now noticed the information described in the above publication that the training with the flow of blood kept blocked is effective. However, according to the common knowledge in general sports and training, it is important how efficiently the flow of blood to the muscles is to be accelerated to supply oxygen and thereby early eliminate lactic acid as a cause of fatigue. Accordingly, the above information is opposite to this common knowledge, and it is felt that the above information has hitherto been unnoticed and rather ignored. Further, there is a fear from a medical point of view that blocking of the flow of blood may bring about a danger to a living body.

As to a general problem in muscle training, conventional muscle training is carried out as an auxiliary muscle training intended to become useful for a desired sport. That is, the conventional muscle training is carried out separately from the desired sport. As far as the present inventor knows, there exists no combination of muscle training with a desired sport to be simultaneously carried out.

SUMMARY OF THE INVENTION

In the above circumstances, the present inventor has examined the conditions of blocking the blood flow for the effectiveness of muscle strengthening as a training method for general sports, and also has examined training tools suitable for effecting the strengthening of the muscles as practicing various types of muscle training, then achieving the present invention.

It is a primary object of the present invention to provide a training tool and a training method using this training tool which can strengthen a desired part of muscles while an intended sport is being carried out. That is, any special training prepared for the intended sport is not required to be separately carried out. In a bicycle sport, for example, the muscles can be strengthened while pedaling a bicycle. Further, in any other sports such as rugby, football, skiing, skating, swimming, and sumo, the muscles can be strengthened while carrying out any intended sport.

Thus, according to the present invention, any special training prepared for the intended sport can be omitted. Accordingly, the training tool and the training method using it have a great advantage for any person doing sports.

The tightening tool according to the present invention is designed to form a tightening loop. The tightening loop is used to surround an arm near a shoulder joint, for example, in a tightened condition. While maintaining this tightened condition, muscle training for the arm is performed by using a dumbbell, for example. As a result, a training effect with use of a light dumbbell can be made similar to that with use of a heavy dumbbell. Furthermore, a training time can be shortened. In addition, any troubles such as an adverse effect to unintended muscles and a damage to joints can be effectively avoided.

While the cause of an increase in such a training effect by the use of the tightening tool is not fully apparent, the following mechanism may be considered.

As is well known, the strengthening of muscles is effected by so-called "super-recovery", or such a phenomenon that while the muscles fatigued through training are being recovered from fatigue, the condition of the muscles exceeds the initial condition. Accordingly, a training efficiency can be increased by providing the conditions for efficiently generating fatigue due to training.

The fatigue of muscles is largely related to the supply of energy sources and oxygen to the muscles and the treatment of lactic acid generated in the course of energy metabolism. Further, these operations are largely dependent upon the flow of blood to the muscles. Accordingly, the fatigue can be efficiently generated in a desired part of the muscles by moderately blocking the flow of blood to the desired part with use of the tightening tool.

Preferably, the tightening tool is provided with an indicating means for indicating a tightening force. According to this structure, an optimum tightening force to be exerted by the tightening tool can be visually confirmed, and the same tightening force can be easily reproduced at all times.

Further, it is also preferable to provide a lining on the surface of the tightening tool contacting with a human skin, so as to protect the skin and absorb sweat. The lining is preferably formed of a material moderately having a softness, breathability, and moisture absorbency.

Other objects, advantages, features, and uses of the invention will be more fully understood from the following detailed description of the preferred embodiments when taken with the accompanying drawings. Further, it should be appreciated that various modifications and changes of the preferred embodiments may be made without departing from the spirit and scope of the invention as defined by the appended claims.

Further, it is to be noted that the term "muscular strength" used in the above and following description has a meaning equivalent to that of "muscle or muscles".

DETAILED DESCRIPTION OF THE PREFERRED EMBODIMENTS

Figure 1:
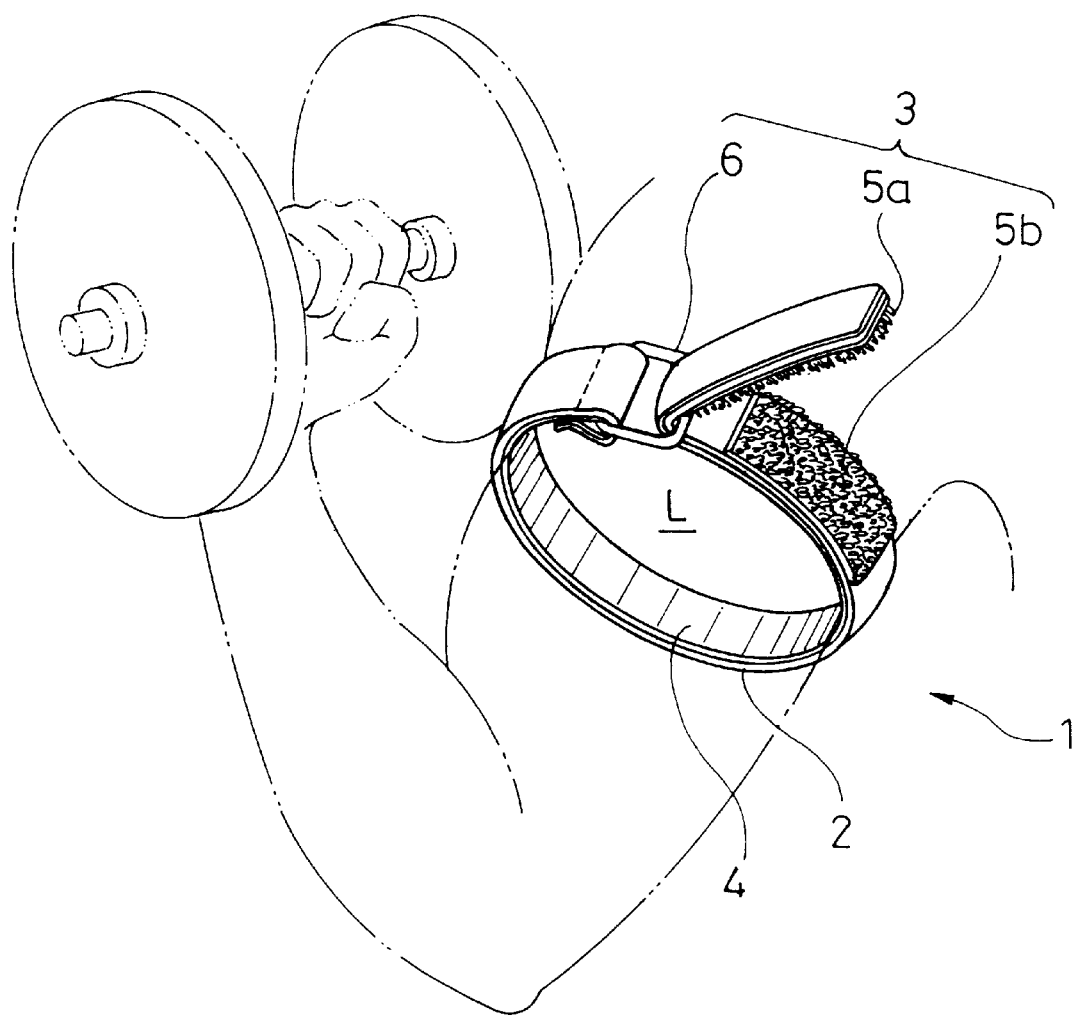
FIG. 1 is a perspective view of a tightening tool according to a first preferred embodiment of the present invention.

Some preferred embodiments of the present invention will now be described with reference to the drawings.

In the following description and the drawings, common parts in the preferred embodiments will be denoted by the same reference numerals and double description thereof will be omitted as required.

First Preferred Embodiment (FIG. 1)

Reference numeral 1 generally denotes a tightening tool according to a first preferred embodiment. The tightening tool 1 is composed of a body 2 and a locking means 3. The body 2 is formed as a belt of an elastic material such as rubber. The body 2 is provided with a lining 4 adapted to come into direct contact with a human skin. The lining 4 is formed of a material having a high elasticity and a high water absorbency.

The locking means 3 is composed of a pair of first and second fastener strips 5a and 5b formed at one end portion of the body 2 and a rectangular holding ring 6 attached to the other end portion of the body 2 by sewing. The tightening tool 1 thus constructed is used in the following manner. The portion of the body 2 at which the first fastener strip 5a is formed is passed through the holding ring 6. Then, the body 2 is folded at a suitable portion to bring the first fastener strip 5a into opposed relationship to the second fastener strip 5b. In this condition, the first fastener strip 5a is pressed on the second fastener strip 5b to be fastened together. As a result, a tightening loop L with a desired diameter is formed inside the lining 4 of the body 2 so as to surround a desired part of a human body. Thus, the desired part can be tightened by the tightening tool 1 with desired tightening force, and such a tightened condition can be maintained.

While FIG. 1 shows a condition that a part between a deltoid muscle and a biceps muscle of arm of the human body is tightened by the tightening tool 1, this condition is merely illustrative and the tightening tool 1 may be, of course, applied to various other parts of the human body. Further, the size of the tightening tool 1 is not limited. Furthermore, some tightening tools 1 may be suitably combined in such a way that they are crossed to be applied to both shoulders of the human body. In addition, the body 2 may be suitably designed in color, pattern, shape, etc. to obtain a good appearance fit for the scene of sports or training.

To confirm the effect of the tightening tool 1 mentioned above, training was subjected to a group of persons using the tightening tool 1 and another group of persons not using the tightening tool 1. The training was carried out by each person for an hour a day and was repeated twice a week for six months. Such an hour training was comprised of barbell curl and reverse push up. The tightening tool 1 was applied between the deltoid muscle and the biceps muscle of arm. The circumferential size of the biceps muscle of arm was measured before and after the six-month training to confirm the result : the muscular strengthening effect on the circumferential sizes in the group using the tightening tool 1 was about three times those in the group not using the tightening tool 1. This result proves that the tightening tool 1 is effective for strengthening of the muscle.

Figure 2:
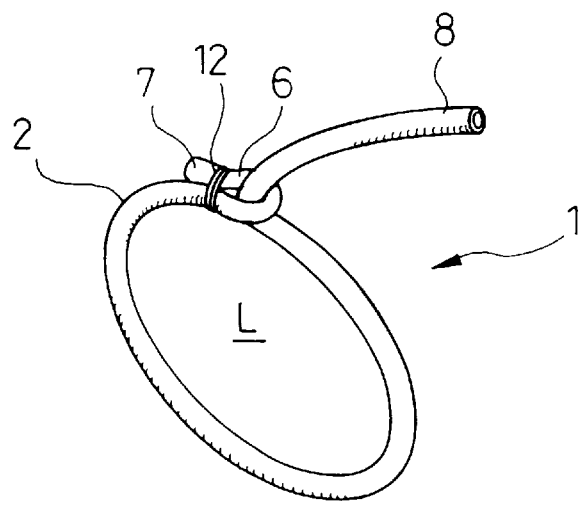
FIG. 2 is a perspective view of a tightening tool according to a second preferred embodiment of the present invention.

Second Preferred Embodiment (FIG. 2)

In this preferred embodiment, a hollow cylindrical, rubber tube having a suitable thickness is used as the body 2 to provide a simple structure. One end portion 7 of the body 2 is turned back to be fixed by winding a string 12 around the body 2, thus forming a holding ring 6 as a locking means. The holding ring 6 has an inner diameter somewhat smaller than an outer diameter of the rubber tube. The other end portion 8 of the body 2 is forcibly inserted through the holding ring 6 to thereby form a tightening loop L inside the body 2. In operation, the other end portion 8 inserted through the holding ring 6 is suitably drawn out to thereby elastically deform the holding ring 6 and a part of the other end portion 8 contacting with the inside surface of the holding ring 6. Accordingly, a contact area and a contact strength between the holding ring 6 and this part of the other end portion 8 are increased to obtain a large frictional force exerted between the rubber surfaces. As a result, the tightening loop L can be maintained at a desired size.

Figure 3:
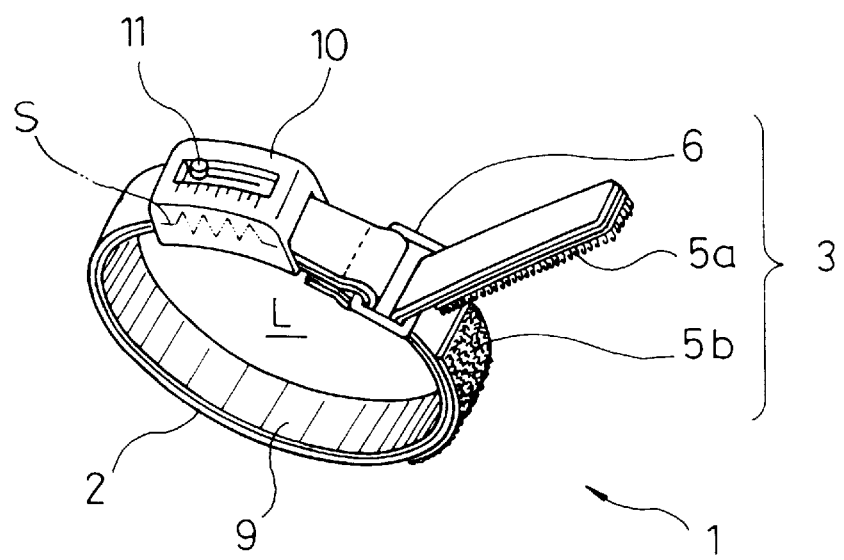
FIG. 3 is a perspective view of a tightening tool according to a third preferred embodiment of the present invention.

Third Preferred Embodiment (FIG. 3)

In this preferred embodiment, an indicating means 10 for indicating tightening force is connected to the body 2, and the structure of the locking means 3 is basically similar to that in the first preferred embodiment. The body 2 is formed as a belt of an inextensible material such as a cloth belt, and a nonwoven fabric 9 as a lining is attached to the inside surface of the body 2 to protect the human skin and provide a feel of comfortable touch. In this preferred embodiment, a spring S is used in the indicating means 10, and the body 2 is separated into two parts at the indicating means 10, wherein opposed ends (not shown) of the two separate parts of the body 2 are connected to both ends of the spring S. The quantity of deformation of the spring S is indicated as a displacement of a pointer 11 connected to the spring S. As another embodiment of the indicating means 10, means for electrically detecting tightening force and indicating a result of detection may be used. In this case, only a detecting portion for detecting the tightening force may be provided on the body 2, and an indicating portion may be connected through a connecting cord to the detecting portion and be provided separately from the body 2, thereby lightening the weight of the tightening tool 1. As still another embodiment of the indicating means 10, any mark such as a scale may be provided on the outside surface of the body 2, thereby further lightening the weight and simplifying the structure.

As described above, the tightening tool for muscle training according to the present invention functions to moderately block the flow of blood to a target muscle to be strengthened and thereby efficiently generate fatigue in the target muscle. Accordingly, by carrying out the muscle training in this condition, a training time can be reduced, and simultaneously any troubles such as an adverse effect to other unintended muscles and a damage to joints can be effectively avoided.

Further, the tightening tool according to the present invention includes the locking means capable of locking the tightening loop at a desired size by a simple operation. Accordingly, a proper tightening force can be desirably obtained, and a troublesome operation for tightening can be eliminated.

Further, when the tightening tool is equipped with the indicating means for indicating a tightening force, the tightening force can be easily monitored by sight, and proper tightening force can be easily reproduced at all times.

Further, when the lining for protecting the human skin is attached to the inside surface of the body of the tightening tool, the human skin can be protected from damage, and a feel of comfortable touch can be obtained.

Fourth Preferred Embodiment

The tightening tool as shown in FIG. 1 was used to carry out training for strengthening the muscles of an upper arm and a thigh.

The body of the tightening tool used for the upper arm was formed as an elastic neoprene belt having a width of 25 mm and a thickness of 3 mm, and the body of the tightening tool used for the thigh was formed as an elastic neoprene belt having a width of 38 mm and a thickness of 3 mm. A Velcro fastener was attached to each body to form the locking means, so as to easily form the tightening loop by a simple operation.

Fifty men aged 19 to 45 were selected as a subject for muscle training, and the tightening tools were applied to a thinner one of a pair of right and left upper arms of each man and a thinner one of a pair of right and left thighs of each man. The reason why the thinner upper arm and the thinner thigh were selected is that they are weaker in muscular strength than the thicker upper arm and the thicker thigh, respectively.

In more detail, the tightening tool for the upper arm was applied between a deltoid muscle and a biceps muscle of arm of each man, and the tightening tool for the thigh was applied between a quadriceps muscle of thigh/a biceps muscle of thigh and a greatest gluteal muscle of each man. The subject parts of the muscles were tightened by the tightening tools for about 30 minutes to block the flow of blood. Since the conditions of the muscles of all the men are different, of course, the tightening time was set especially in consideration of arm and thigh thicknesses, condition of fat put on, age, muscle thickness depending upon experience of exercise, condition of health (any men other than one prohibited from doing sports by a doctor was permitted to carry out this training), etc. In particular, in the event that the fingers of the hand or the foot were numbed to lose sensation, the tightened condition was immediately released to end the muscle training.

A degree of tightening was determined so that a condition where the blood vessel in the back of the hand or the instep rose was proper, whereas a condition where this blood vessel did not rise at all was improper because of excess of tightening.

The exercise carried out for the arm during the tightening time was a type of exercise such that a dumbbell was lifted to contract the muscle of the arm and the dumbbell was then lowered to relax the muscle of the arm. On the other hand, the exercise carried out for the thigh during the tightening time was a squat type of exercise.

This muscle training was carried out for 30 minutes a day, and was repeated three times a weak every other day for two weeks, i.e., totally six times for two weeks. After the two weeks, the muscles of the arm and the thigh of each man tightened with the tightening tools were compared with those not tightened with the tightening tools. As the result of comparison, the muscles subjected to the muscle training with use of the tightening tools were enlarged by 5%.

This result shows that the muscular strength was greatly increased in a short period of time by the muscle training according to the present invention as compared with the conventional muscle training.

Fifth Preferred Embodiment

Muscle training similar to that in the fourth preferred embodiment with the exception that the tightening time was set within about 15 minutes and no exercise such as the lifting/lowering of a dumbbell and the squat type of exercise was carried out with the tightened condition maintained. After the two-week total training, the muscles of the arm and the thigh tightened were compared with those not tightened, and it was confirmed that the muscles subjected to the muscle training with use of the tightening tools were increased by 2%.

Sixth Preferred Embodiment

With use of a tightening tool similar to that used in the fourth preferred embodiment, training for strengthening the muscle of the thigh was carried out as a bicycle sport being carried out.

Ten men aged from 19 to 32 were selected as a subject for the bicycle sport, and the tightening tool was applied to a thinner one of both thighs of each man at a position between a quadriceps muscle of thigh/a biceps muscle of thigh and a greatest gluteal muscle.

The subject part was tightened by the tightening tool for about 30 minutes to block the flow of blood. In the event that the fingers of the foot were numbed to lose sensation, the tightened condition was immediately released to end the muscle training.

This muscle training with the bicycle sport was carried out for 30 minutes a day, and was repeated three times a week every other day for two weeks, i.e., totally six times for two weeks. After the two weeks, the muscle of the thigh of each man tightened by the tightening tool was compared with that not tightened by the tightening tool of each man. As the result of comparison, the muscle subjected to the muscle training with use of the tightening tool was enlarged by 5%.

This result shows that the muscular strength was greatly increased in a short period of time as compared with the conventional muscle training by incorporating the muscle training into the exercise as the bicycle sport without carrying out a special muscle training separately from an intended sport.

What is claimed is:

1. A muscle training method, comprising: providing around a desired part of a user's muscles a tightening tool for muscle training, said tightening tool comprising an elastic body in the form of a belt, rope, or tube, for forming a tightening loop adapted to surround the desired part of muscles and to tighten the muscle to block a flow of blood thereto, and locking means for holding said tightening loop at a desired size; and using said tightening tool to accelerate enlargement of muscles by tightening the desired part of muscles to such a degree as to block a flow of blood to the desired part, and maintaining a tightened condition of the desired part by said tightening tool for about 15 minutes or less without carrying out any exercise to accelerate enlargement of the muscles.

* * * * *